US005972237A

United States Patent [19]

Müller et al.

[11] Patent Number: 5,972,237
[45] Date of Patent: Oct. 26, 1999

[54] USE OF HETEROCYCLIC COMPOUNDS AS ACTIVATORS FOR INORGANIC PEROXY COMPOUNDS

[75] Inventors: Reinhard Müller, Friedelsheim; Thomas Wehlage, Speyer; Wolfgang Trieselt, Karlsruhe; Alfred Oftring, Bad Dürkheim; Elisabeth Kappes, Limburgerhof; Günter Oetter, Frankenthal; Dieter Boeckh, Limburgerhof; Roland Ettl, Hassloch; Albert Hettche, Hessheim, all of Germany

[73] Assignee: BASF Aktiengesellschaft, Ludwigshafen, Germany

[21] Appl. No.: 08/952,076

[22] PCT Filed: May 4, 1996

[86] PCT No.: PCT/EP96/01863

§ 371 Date: Nov. 17, 1997

§ 102(e) Date: Nov. 17, 1997

[87] PCT Pub. No.: WO96/36686

PCT Pub. Date: Nov. 21, 1996

[30] Foreign Application Priority Data

May 17, 1995 [DE] Germany .......................... 195 18 039

[51] Int. Cl.$^6$ ................................ C11D 3/39; A61L 2/18

[52] U.S. Cl. ................................ 252/186.39; 252/186.4; 423/584; 540/451; 540/454; 540/488; 540/524; 540/525; 544/96; 544/97; 546/188; 546/189; 546/207; 546/208; 548/230; 548/524; 548/551; 549/266; 549/291; 549/292; 549/295; 549/320; 549/322

[58] Field of Search .................................... 540/451, 454, 540/488, 524, 525; 544/96, 97; 546/188, 189, 207, 208; 548/230, 524, 551; 549/266, 291, 292, 295, 320, 322; 252/186.39, 186.4; 423/584

[56] References Cited

FOREIGN PATENT DOCUMENTS

| | | |
|---|---|---|
| 0 028 432 | 5/1981 | European Pat. Off. . |
| 0 659 876 | 6/1995 | European Pat. Off. . |
| 0 677 576 | 10/1995 | European Pat. Off. . |
| 0 690 122 | 1/1996 | European Pat. Off. . |
| 0 699 745 | 3/1996 | European Pat. Off. . |
| 0 713 910 | 5/1996 | European Pat. Off. . |
| 2 388 924 | 11/1978 | France . |
| WO A 94 27970 | 12/1994 | WIPO . |
| WO A 94 28103 | 12/1994 | WIPO . |
| WO A 94 28105 | 12/1994 | WIPO . |
| WO A 95 14759 | 6/1995 | WIPO . |
| WO A 95 17497 | 6/1995 | WIPO . |
| WO A 95 17498 | 6/1995 | WIPO . |
| WO A 95 27773 | 10/1995 | WIPO . |
| WO A 95 28463 | 10/1995 | WIPO . |
| WO A 96 16157 | 5/1996 | WIPO . |

OTHER PUBLICATIONS

CA 120: 106829, 1993.
CA 121: 17822, 1993.
CA 111: 115118, 1989.
CA 98: 160816, 1982.

*Primary Examiner*—Richard L. Raymond
*Attorney, Agent, or Firm*—Oblon, Spivak, McClelland, Maier & Neustadt, P.C.

[57] ABSTRACT

Heterocyclic compounds I $R^1$—X—L (I)

where
L is a cyclic carbamate residue, a lactonoxy residue or a lactam residue,
X is an oxygen-containing group

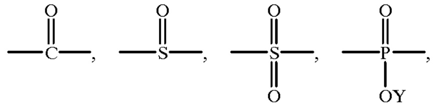

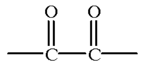
or
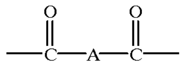

where A is a linker, and
$R^1$ is an organic radical or a group L,
are used as activators for inorganic peroxy compounds, in particular as cold bleach activators or optical brighteners in detergents, cleaners and bleaches and in disinfectants.

13 Claims, No Drawings

USE OF HETEROCYCLIC COMPOUNDS AS ACTIVATORS FOR INORGANIC PEROXY COMPOUNDS

This application is a 371 of PCT/EP96/01863, filed Apr. 1996.

BACKGROUND OF THE INVENTION

1. Field of the Invention

The present invention relates to the use of certain heterocyclic compounds based on cyclic carbamates, lactones or lactams as activators for inorganic peroxy compounds, in particular as cold bleach activators or optical brighteners in detergents, cleaners and bleaches and in disinfectants. The present invention furthermore relates to certain industrial formulations which contain these heterocyclic compounds.

2. Description of the Background

In the efforts to achieve energy-saving washing, cleaning and bleaching processes, recently use temperatures in the lower temperature range have become increasingly important, for example for textile laundering distinctly below 60° C., and in particular below 45° C. However, at these temperatures, the effect of the known activators for inorganic peroxy compounds, this being the system responsible for the bleaching or cleaning action, decreases markedly. There has thus been no lack of attempts to develop more effective activators for this temperature range, without any convincing success to date.

EP-A 028 432 discloses textile detergent formulations which contain, among other things, N-acyllactams, eg. N-acetylcaprolactam, as precursor for a bleaching organic peroxy acid.

SUMMARY OF THE INVENTION

It is an object of the present invention to improve the bleaching, oxidizing and cleaning action of a system comprising activator and inorganic peroxy compounds in the lower temperature range, in particular from 15 to 60° C.

We have found that this object is achieved by using heterocyclic compounds of the general formula I $$R^1—X—L \qquad (I)$$

where

L is (a) a cyclic carbamate residue of the formula

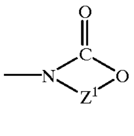

(b) a lactonoxy residue of the formula

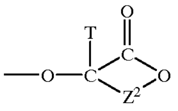

or (c) a lactam residue of the formula

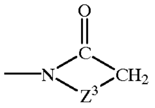

where $Z^1$ to $Z^3$ are 1,2-, 1,3-, 1,4- or 1,5-alkylene groups which have 2 to 20 carbon atoms and which can additionally be functionalized by one to three hydroxyl groups, $C_1$–$C_4$-alkoxy groups, amino groups, $C_1$–$C_4$-alkylamino groups, di-$C_1$–$C_4$-alkylamino groups, chlorine atoms, bromine atoms, nitro groups, cyano groups, carboxyl groups, sulfo groups, carboxy-$C_1$–$C_4$-alkyl groups, carboxamide groups or phenyl, tolyl or benzyl radicals, it being possible for aromatic nuclei in turn likewise to be substituted by the said radicals, or can be interrupted by one or two non-adjacent oxygen atoms, amino groups, $C_1$–$C_4$-alkylamino groups or carbonyl groups, and T is hydrogen or $C_1$–$C_4$-alkyl, X is an oxygen-containing group of the formula

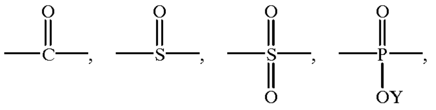

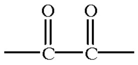

or

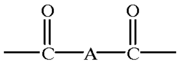

where

Y is hydrogen, ammonium which may be substituted by organic radicals, or $C_1$–$C_4$-alkyl, and A is a $C_1$–$C_{18}$-alkylene group, a $C_2$–$C_{18}$-alkenylene group, a $C_5$–$C_{32}$-cycloalkylene group, a $C_7$–$C_{30}$-aralkylene group,. a $C_6$–$C_{18}$-arylene group or a $C_3$–$C_{18}$-hetarylene group, it being possible for aliphatic structural units additionally to be functionalized by one to five hydroxyl groups, $C_1$–$C_4$-alkoxy groups, amino groups, $C_1$–$C_4$-alkylamino groups, di-$C_1$–$C_4$-alkylamino groups, chlorine atoms, bromine atoms, nitro groups, cyano groups, carboxyl groups, sulfo groups, carboxy-$C_1$–$C_4$-alkyl groups, carboxamide groups or phenyl, tolyl or benzyl radicals, where aromatic, cycloaliphatic and heteroaromatic structural units can likewise be substituted by the said radicals, or to be interrupted by one to eight non-adjacent oxygen atoms, amino groups, $C_1$–$C_4$-alkylamino groups or carbonyl groups, and $R^1$ in the case of a cyclic carbamate residue (a), of a lactonoxy residue (b), of a lactam residue (c) in which the group $Z^3$ is a 1,2-, 1,3- or 1,5-alkylene group which has 2 to 20 carbon atoms, and which can additionally be functionalized or interrupted by the radicals or atoms indicated above, and of a lactam residue (c) in which the group $Z^3$ is a 1,4-alkylene group which has 4 to 20 carbon atoms and which can likewise additionally be functionalized or interrupted by the radicals or atoms indicated above, and in which, at the same time, the group X connected thereto is —SO—, —$SO_2$—, —PO(OY)—, —CO—CO— or —CO—A—CO—, has the following meaning:

$C_1$–$C_{30}$-alkyl, $C_2$–$C_{30}$-alkenyl, $C_5$–$C_{18}$-cycloalkyl, $C_7$–$C_{18}$-aralkyl, $C_6$–$C_{18}$-aryl or $C_3$–$C_{18}$-hetaryl, it being possible for aliphatic radicals additionally to be functionalized by one to five hydroxyl groups, $C_1$–$C_4$- alkoxy groups, amino groups, $C_1$–$C_4$-alkylamino groups, di-$C_1$–$C_4$-alkylamino groups, chlorine atoms, bromine atoms, nitro groups, cyano groups, carboxyl groups, sulfo groups, carboxy-$C_1$–$C_4$-alkyl groups, carboxamide groups or phenyl, tolyl or benzyl radicals, where aromatic, cycloaliphatic and heteroaromatic structural units can likewise be substituted by the said radicals, or to be interrupted by one to eight non-adjacent oxygen atoms, amino groups, $C_1$–$C_4$-alkylamino groups or carbonyl groups, or a heterocyclic radical L or a group of the formula —$OR^2$, —$NHR^2$, —NH—CO—$R^2$, —$N(R^2)^2$ or —$N(CO—R^2)^2$, where $R^2$ is $C_1$–$C_{30}$-alkyl, $C_2$–$C_{30}$-alkenyl, $C_5$–$C_{18}$-cycloalkyl, $C_7$–$C_{18}$-aralkyl, $C_6$–$C_{18}$-aryl or $C_3$–$C_{18}$-hetaryl, which can in each case be functionalized or interrupted as indicated under $R^1$, and $R^1$ in the case of a lactam residue (c) in which the group $Z^3$ is a 1,4-alkylene group which has 4 to 20 carbon atoms and which can additionally be functionalized or interrupted by the radicals or atoms indicated above, and in which, at the same time, the group X connected thereto is —CO—, has the following meaning:

$C_9$–$C_{30}$-alkyl, $C_2$–$C_{30}$-alkenyl, $C_5$–$C_{18}$-cycloalkyl, $C_7$–$C_{18}$-aralkyl, $C_{10}$–$C_{18}$-aryl or $C_3$–$C_{18}$-hetaryl, it being possible for aliphatic radicals additionally to be functionalized by one to five hydroxyl groups, $C_1$–$C_4$-alkoxy groups, amino groups, $C_1$–$C_4$-alkylamino groups, di-$C_1$–$C_4$-alkylamino groups, chlorine atoms, bromine atoms, nitro groups, cyano groups, carboxyl groups, sulfo groups, carboxy-$C_1$–$C_4$-alkyl groups, carboxamide groups or phenyl, tolyl or benzyl radicals, where aromatic cycloaliphatic and heteroaromatic structural units can likewise be substituted by the said radicals, or to be interrupted by one to eight non-adjacent oxygen atoms, amino groups, $C_1$–$C_4$-alkylamino group or carbonyl groups, or a heterocyclic radical L or a group of the formula —$OR^2$, —$NHR^2$, —NH—CO—$R^2$, —$N(R^2)^2$ or —$N(CO—R^2)^2$, where $R^2$ is $C_1$–$C_{30}$-alkyl, $C_2$–$C_{30}$-alkenyl, $C_5$–$C_{18}$-cycloalkyl, $C_7$–$C_{18}$-aralkyl, $C_6$–$C_{18}$-aryl or $C_3$–$C_{18}$-hetaryl, which can in each case be functionalized or interrupted as indicated under $R^1$, as activators for inorganic peroxy compounds.

The variables $Z^1$ to $Z^3$ in the heterocyclic systems (a) to (c) can be, in particular, $C_2$–$C_{10}$-alkylene groups of the following structure:

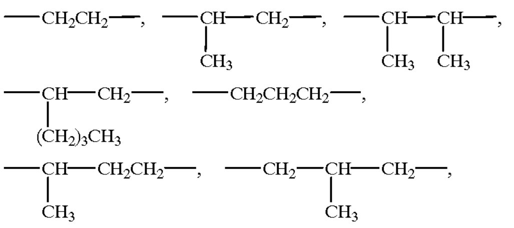

-continued

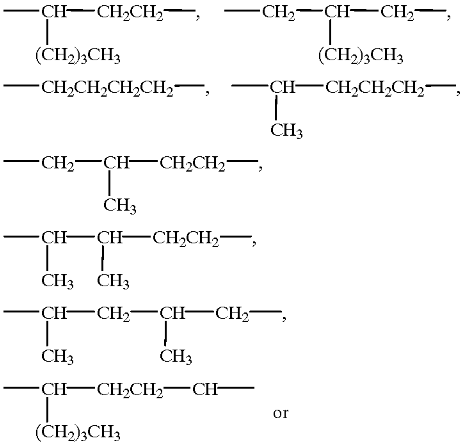

or $—CH_2CH_2CH_2CH_2CH_2—$, where in the case of asymmetric alkylene groups both possibilities for incorporation into the rings are possible in principle. The variables $Z^1$ to $Z^3$ can be functionalized or interrupted as stated.

Typical examples of the linker A are the following:

as linear or branched $C_1$–$C_{18}$-alkylene group, in particular $C_6$–$C_{12}$-alkylene group, possibilities are methylene, 1,2-ethylene, 1,1-ethylene, 1,3-propylene, 1,2-propylene, 1,1-propylene, 2,2-propylene, 1,4-butylene, 1,2-butylene, 2,3-butylene, pentamethylene, 3-methyl-1,5-pentylene, hexamethylene, heptamethylene, octamethylene, nonamethylene, decamethylene, undecamethylene, dodecamethylene, tetradecamethylene, hexadecamethylene or octadecamethylene;

as linear or branched $C_2$–$C_{18}$-alkenylene group, in particular $C_6$–$C_{12}$-alkenylene group, possibilities are linkers having one, two or three olefinic double bonds, eg. 1,2-ethenylene, 1,3-propenylene, 1,4-but-2-enylene, 1,6-hex-3-enylene, 1,8-oct-4-enylene or 1,12-dodec-6-enylene;

suitable $C_5$–$C_{32}$-cycloalkylene groups, in particular $C_5$–$C_{10}$-cycloalkylene groups, are 1,2- or 1,3-cyclopentylene, 1,2-, 1,3- or 1,4-cyclohexylene, 1,2-, 1,3- or 1,4-cycloheptylene, 1,2-, 1,3-, 1,4- or 1,5-cyclooctylene or groups of the formula

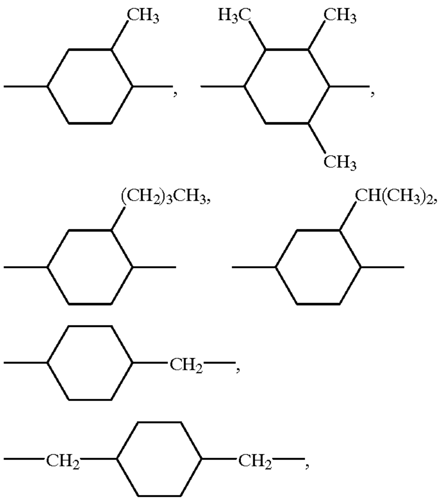

-continued

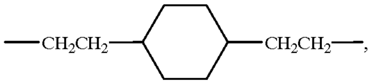

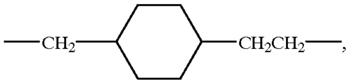

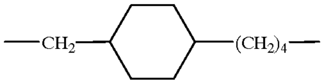 or

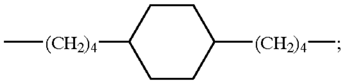

suitable $C_7$–$C_{30}$-aralkylene groups, in particular unsubstituted or alkyl-substituierte $C_7$–$C_{22}$-phenylalkylene and -diphenyl-alkylene groups, are groups of the formula

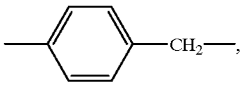

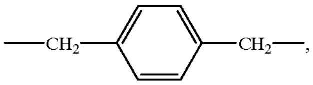

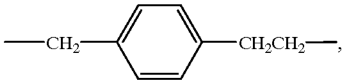

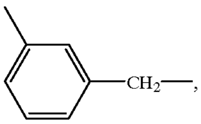 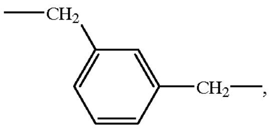

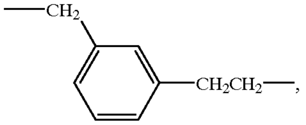

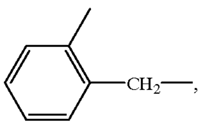 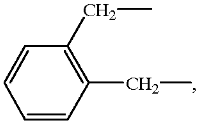

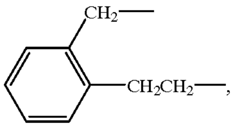 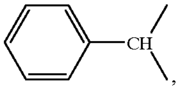

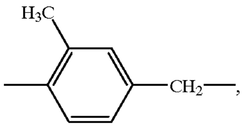

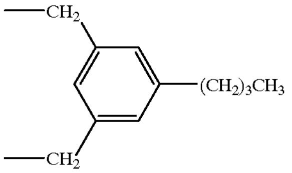 or

-continued

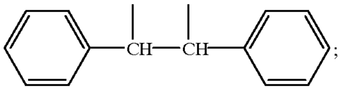

particularly suitable $C_6$–$C_{18}$-arylene groups, in particular unsubstituted or alkyl-substituted phenylene, bisphenylene or naphthylene groups, are 1,4-, 1,3- and 1,2-phenylene, but also groups of the formula

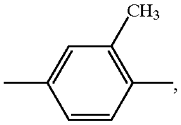 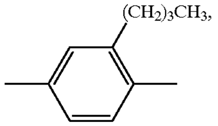

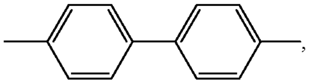

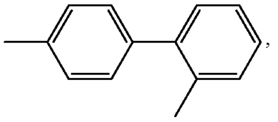 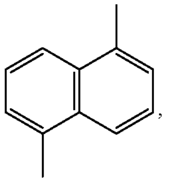

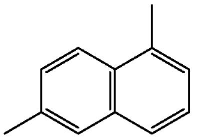 or 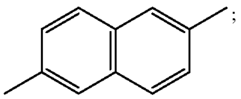

suitable $C_3$–$C_{18}$-hetarylene groups, in particular 5- or 6-membered $C_3$–$C_{12}$-hetarylene groups having one or two heteroatoms from the group consisting of nitrogen, oxygen and sulfur, are groups of the formula

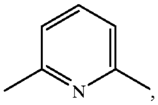 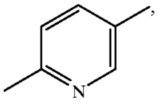

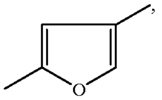 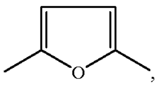

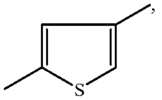 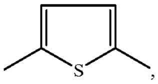

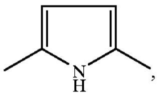 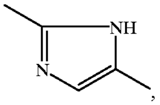

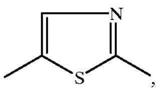 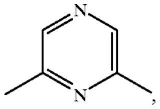

-continued

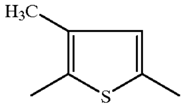

or

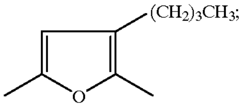

examples of suitable structures interrupted by oxygen or amino groups, in particular NH or $N(CH_3)$ groups, are the following structures:

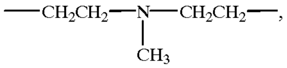

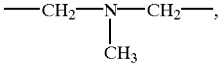 $-CH_2-O-CH_2-$, $-CH_2CH_2-O-CH_2-$, $-CH_2CH_2-O-CH_2CH_2-$, $-CH_2CH_2-(O-CH_2CH_2)_n-$, $-(CH_2)_4-O-(CH_2)_4-$,

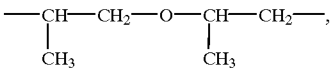

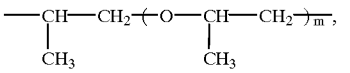

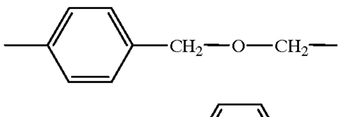 or

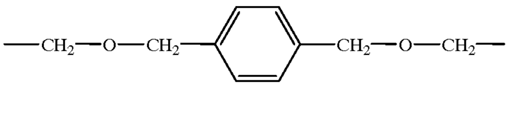

with n=2 to 8 and m=2 to 5.

Suitable meanings for the radicals $R^1$ and $R^2$ are the following:

suitable as $C_1$–$C_{30}$-alkyl or $C_9$–$C_{30}$-alkyl group are, for example, methyl, ethyl, n-propyl, isopropyl, n-butyl, isobutyl, sec-butyl, tert-butyl, n-pentyl, isopentyl, sec-pentyl, tert-pentyl, neopentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl; $C_1$–$C_{12}$-alkyl and $C_9$–$C_{12}$-alkyl groups are preferred;

suitable as $C_2$–$C_{30}$-alkenyl group are, for example, vinyl, allyl, 2-methylprop-2-enyl or the corresponding radical derived from oleic acid, linoleic acid or linolenic acid; $C_2$–$C_6$-alkenyl and $C_{16}$–$C_{22}$-alkenyl groups are preferred;

particularly suitable as $C_5$–$C_{18}$-cycloalkyl group are $C_5$–$C_{10}$-cycloalkyl groups, eg. cyclopentyl, cyclohexyl, 2-, 3- or 4-methylcyclohexyl, 2,3-, 2,4-, 2,5- or 2,6-dimethylcyclohexyl, cycloheptyl or cyclooctyl;

suitable as $C_7$–$C_{18}$-aralkyl, in particular $C_7$–$C_{12}$-aralkyl, group are, in particular, alkyl-substituted phenylalkyl groups, eg. benzyl; 2-, 3- or 4-methylbenzyl, 2-phenylethyl, 3-phenylpropyl, 4-phenylbutyl, 2-, 3- or 4-ethylbenzyl, 3- or 4-isopropylbenzyl or 3- or 4-butylbenzyl;

suitable as $C_6$–$C_{18}$-aryl or $C_{10}$–$C_{18}$-aryl group are, for example, phenyl, 2-, 3- or 4-bisphenyl, α- or β-naphthyl, 2-, 3- or 4-methylphenyl, 2-, 3- or 4-ethylphenyl, 3- or 4-isopropylphenyl, 3- or 4-butylphenyl or 3- or 4-(2'-ethylhexyl)phenyl; $C_6$–$C_{14}$-aryl and $C_{10}$–$C_{14}$-aryl groups are preferred, in particular in the former case phenyl and alkyl-substituted phenyl;

suitable as $C_3$–$C_{18}$-hetaryl group are, in particular, 5- or 6-membered $C_3$–$C_{12}$-hetaryl groups having one or two hetero atoms from the group consisting of nitrogen, oxygen and sulfur; examples thereof are:

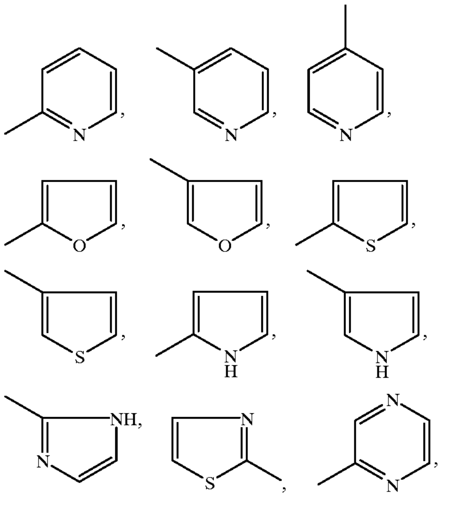

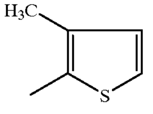

and

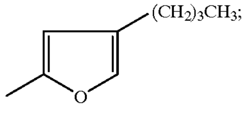

suitable aliphatic radicals interrupted by oxygen or amino groups, in particular NH or $N(CH_3)$ groups are, for example, the following structures:

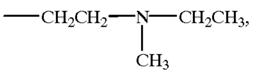 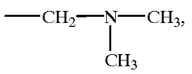

$-CH_2-O-CH_3$, $-CH_2CH_2-O-CH_3$, $-CH_2CH_2-O-CH_2CH_3$, $-CH_2CH_2-(O-CH_2CH_2)_n-OH$, $-(CH_2)_4-O-CH_3$,

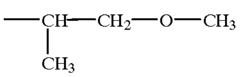 and

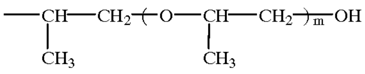

The variables $Z^1$ to $Z^3$, A, $R^1$ and $R^2$ defined above may additionally be functionalized by the stated groups. In this case, $C_1$–$C_4$-alkoxy groups are, in particular, methoxy, ethoxy, n-propoxy, isopropoxy, n-butoxy, isobutoxy, sec-butoxy or tert-butoxy. Preferred amino groups are $-NH_2$, $-NH(CH_3)$, $-NH(CH_2CH_3)$, $-N(CH_3)_2$ and $-N(CH_2CH_3)_2$. Examples of carboxy-$C_1$–$C_4$-alkyl groups are carboxymethyl, carboxyethyl, carboxypropyl, carboxybutyl and carboxytert-butyl.

The oxygen-containing group X in which one or two oxygen atoms are linked by a double bond to carbon, sulfur or phosphorus atoms, ie. represent carbonyl or heterocarbonyl functionalities, is preferably

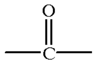

or

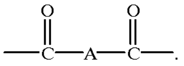

In the case where $R^1$=L, the two heterocyclic radicals L linked to the group X are preferably identical.

The following structural types of heterocyclic compounds I are preferably used:

(1) N-Acyloxazolidones of the formula

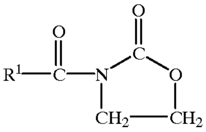

(2) N-Acyl-1,3-tetrahydrooxazinones of the formula

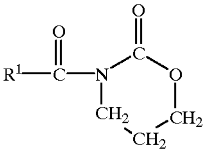

(3) Acyloxy-γ-butyrolactones of the formula

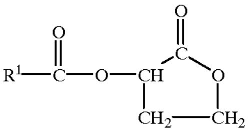

(4) Acyloxy-γ-valerolactones of the formula

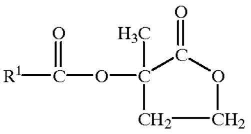

(5) O-Acylpantolactones of the formula

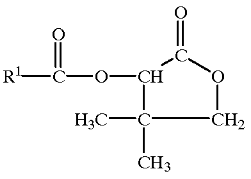

(6) Acyloxy-6-valerolactones of the formula

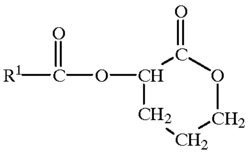

(7) Acyloxy-ϵ-caprolactones of the formula

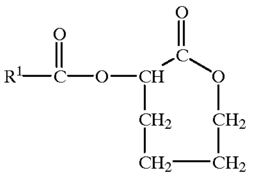

(8) Acyl-γ-butyrolactams of the formula

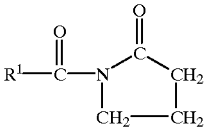

(9) Alkoxy- and aryloxycarbonyl-γ-butyrolactams of the formula

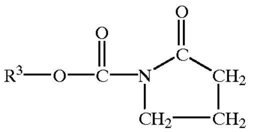

($R^3$ = $C_1$–$C_{12}$-alkyl or $C_6$–$C_{14}$-aryl)

(10) N-Acyl-δ-valerolactams of the formula

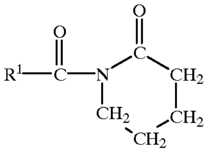

(11) N-Acyl-ϵ-caprolactams of the formula

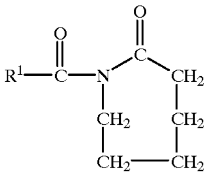

(12) N,N'-Carbonylbisoxazolidone of the formula

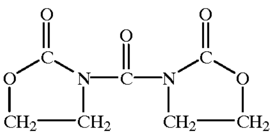

(13) N,N'-Carbonylbis-1,3-tetrahydrooxazinone of the formula

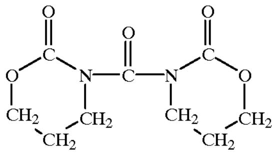

(14) Carbonic acid bis-γ-butyrolactone of the formula

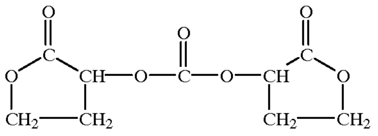

(15) Carbonic acid bis-γ-valerolactone of the formula

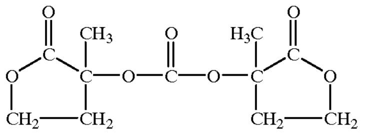

(16) O,O'-Carbonylbispantolactone of the formula

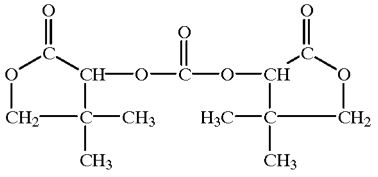

(17) Carbonic acid bis-δ-valerolactone of the formula

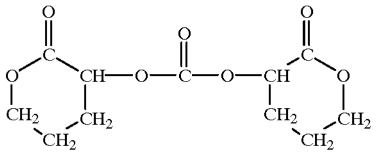

(18) Carbonic acid bis-ε-caprolactone of the formula

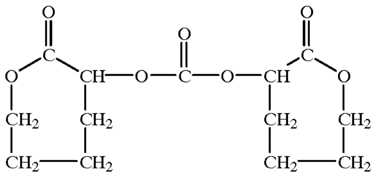

(19) N,N'-Carbonylbis-γ-butyrolactam of the formula

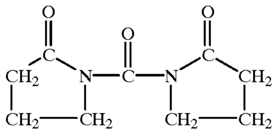

(20) N,N'-Carbonylbis-δ-valerolactam of the formula

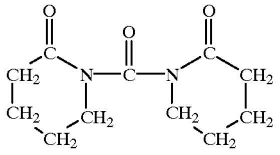

(21) N,N'-Carbonylbis-ε-caprolactam of the formula

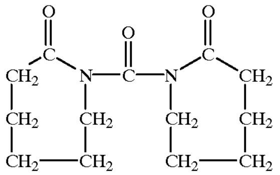

(22) N,N'-Carbonyl-γ-butyrolactam-ε-caprolactam of the formula

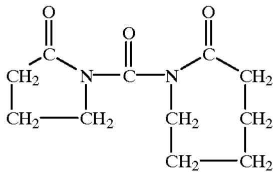

(23) N-(ε-Caprolactam)-carbamic acid O-(pantolactone) of the formula

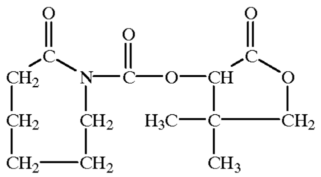

(24) doubled N-acyloxazolidones of the formula

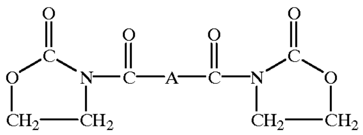

(25) doubled N-acyl-1,3-tetrahydrooxazinones of the formula

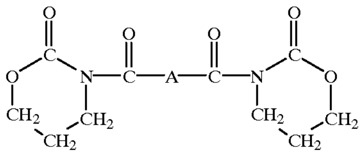

(26) doubled acyloxy-γ-butyrolactones of the formula

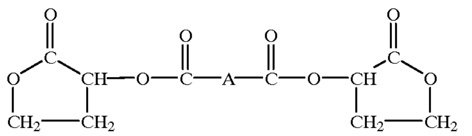

(27) doubled acyloxy-γ-valerolactones of the formula

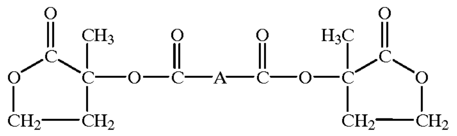

(28) doubled O-acylpantolactones of the formula

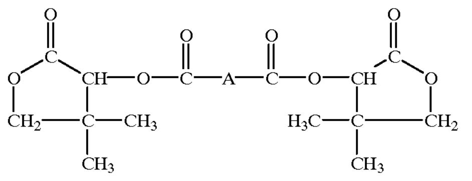

(29) doubled acyloxy-δ-valerolactones of the formula

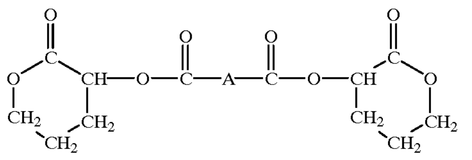

(30) doubled acyloxy-ε-caprolactones of the formula

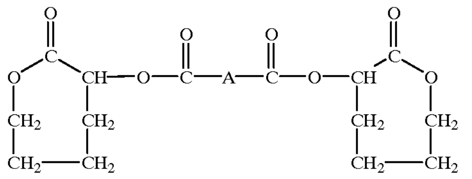

(31) doubled acyl-γ-butyrolactams of the formula

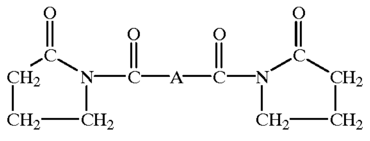

(32) doubled acyl-δ-valerolactams of the formula

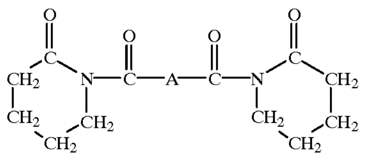

(33) doubled N-acyl-ε-caprolactams of the formula

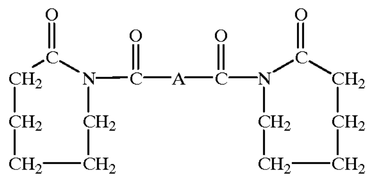

The radical $R^1$ in structural types (1) to (8) and (10) is, in particular, methyl, ethyl, n-butyl, tert-butyl, n-heptyl, n-nonyl, n-undecyl, cyclohexyl, benzyl, phenyl or 2-, 3- or 4-methylphenyl.

The radical $R^1$ in structural type (11) is, in particular, n-nonyl, n-undecyl or cyclohexyl.

The linker A in structural types (24) to (33) is, in particular, hexamethylene, octamethylene, decamethylene, dodecamethylene, 1,3- or 1,4-cyclohexylene or 1,4-, 1,3- or 1,2-phenylene; 1,4-phenylene (derived from terephthalic acid) is of particular interest for A.

When the described heterocyclic compounds I are used according to the invention there is found to be an unexpected increase in the oxidizing, bleaching and cleaning action in aqueous washing, bleaching and cleaning liquors containing inorganic peroxy compounds in the temperature range from 10 to 80° C., in particular 15 to 60° C., especially 20 to 45° C.

The compounds I can be used as activators for inorganic peroxy compounds whenever a particular increase in the oxidizing effect of the inorganic peroxy compounds at low temperatures is important, eg. in bleaching textiles, hair or hard surfaces, in oxidizing organic or inorganic intermediates and in disinfection.

Most of these activators moreover have superior properties to those of activators hitherto disclosed.

The compounds I are substances with a neutral or pleasant odor and can therefore be used without problems even in detergents and cleaners intended for domestic use.

It is important for the use according to the invention to set up conditions under which, for example, hydrogen peroxide and the compounds I are able to react together with the aim of obtaining products with a stronger oxidizing action. These conditions are present in particular when the two reactants come into contact in aqueous alkaline solution.

The conditions may vary widely depending on the purpose of use.

Thus, besides purely aqueous solutions, also suitable as reaction medium are mixtures of water and suitable organic solvents, eg. for use in disinfection or for oxidizing intermediates. The pH of the reaction medium may vary within wide limits from the weakly acidic range (pH 4) to the strongly alkaline range (pH 13), depending on the purpose of use. The alkaline range from pH 8 to pH 11 is preferred because it is particularly advantageous for the activation reaction and the stability of the peroxy compound formed.

For this reason, the described activator is also preferably used together with a sodium perborate or with sodium carbonate perhydrate, which in solution already have pH values in this range. Examples of other suitable peroxy compounds are phosphate perhydrates and urea perhydrate. It may occasionally be expedient to change the pH of the medium once again after the activation reaction has taken place, in particular into the acidic range, by suitable additives.

The amounts of peroxy compounds used are generally chosen so that the solutions contain from 10 to 10,000 ppm active oxygen, preferably from 50 to 5000 ppm active oxygen. The amount of activator used also depends on the purpose of use. Depending on the required degree of activation, from 0.03 to 1.0 mol, preferably 0.1 40 to 0.5 mol, of activator are used per mol of inorganic peroxy compound, but the amounts may also be above or below these limits in special cases.

The compounds I can be used for the activation in pure form or, if this is expedient to increase the storage stability for example, in special forms for marketing, such as tablets, granules or pills. The forms produced by agglomeration granulation are particularly important in this connection. Suitable for machine metering are liquid activators as such or solutions in organic solvents or liquid dispersions which contain the activator.

The agents are preferably used in finished formulations mixed with the peroxy compounds to be activated and, where appropriate, other components necessary for the required bleaching, oxidizing or cleaning process, such as pH regulators and stabilizers for peroxy compounds. It is moreover possible for other conventional activators to be present in addition to the compounds I. Mixing with selected amounts of peroxy compounds and other additives facilitates use, and the required result is obtained more reliably by the user because optimal conditions are set up when the compositions dissolved are without further action. Compositions of this type are in the form of solids, which can preferably be scattered, or of liquids.

Suitable additional activators which can be combined with the compounds are, in particular:

polyacylated sugars, eg. pentaacetylglucose;

acyloxybenzenesulfonic acids and their alkali metal and alkaline earth metal salts, eg. sodium p-isononanoyloxybenzenesulfonate or sodium p-benzoyloxybenzenesulfonate;

N,N-diacylated and N,N,N',N'-tetraacylated amines, eg. N,N,N',N'-tetraacetylmethylenediamine and -ethylenediamine, N,N-diacetylaniline, N,N-diacetyl-p-toluidine or 1,3-diacylated hydantoins such as 1,3-diacetyl-5,5-dimethylhydantoin;

N-alkyl-N-sulfonylcarboxamides, eg. N-methyl-N-mesylacetamide or N-methyl-N-mesylbenzamide;

N-acylated cyclic hydrazides, acylated triazoles or urazoles, eg. monoacetylated maleic hydrazide;

O,N,N-trisubstituted hydroxylamines, eg. O-benzoyl-N,N-succinylhydroxylamine,

O-acetyl-N,N-succinylhydroxylamine or O,N,N-triacetylhydroxylamine;

N,N'-diacylsulfamides, eg. N,N'-dimethyl-N,N'-diacetylsulfamide or N,N'-diethyl-N,N'-dipropionylsulfamide;

triacyl cyanurates, eg. triacetyl cyanurate or tribenzoyl cyanurate;

carboxylic anhydrides, eg. benzoic anhydride, m-chlorobenzoic anhydride or phthalic anhydride;

1,3-diacyl-4,5-diacyloxyimidazolines, eg. 1,3-diacetyl-4,5-di-acetoxyimidazoline;

tetraacetylglycoluril and tetrapropionylglycoluril;

diacylated 2,5-diketopiperazines, eg. 1,4-diacetyl-2,5-diketopiperazine;

products of the acylation of propylenediurea and 2,2-dimethylpropylenediurea, eg. tetraacetylpropylenediurea;

α-acyloxypolyacylmalonamides, eg. α-acetoxy-N,N'-diacetylmalonamide;

diacyldioxohexahydro-1,3,5-triazines, eg. 1,5-diacetyl-2,4-dioxohexahydro-1,3,5-triazine;

benzo-1,3(4H)-oxazin-4-ones with alkyl radicals, eg. methyl, or aromatic radicals, eg. phenyl, in position 2.

It is of particular interest to use the heterocyclic compounds I as cold bleach activators or optical brighteners in detergents, cleaners and bleaches, especially in detergents and bleaches and bleach additives for textile laundering, and in disinfectants.

In the textile laundering sector, the described activators can be combined with virtually all conventional ingredients of detergents and bleaches. It is possible in this way to design compositions which are specifically suitable for textile treatment at low temperatures, as well as those suitable in a plurality of temperature ranges up to the traditional boiling wash.

The main ingredients of detergents, bleaches and cleaners are, besides peroxy compounds and activators, builders, ie. inorganic builders and/or organic cobuilders, and surfactants, in particular anionic and/or nonionic surfactants. It is also possible for other conventional auxiliaries and accompanying substances, such as fillers, complexing agents, phosphonates, dyestuffs, corrosion inhibitors, antiredeposition agents, bleach catalysts, peroxide stabilizers, electrolytes, optical brighteners, enzymes, perfume oils, foam regulators and activating substances, to be present in these compositions if expedient.

Inorganic builders

Suitable inorganic builder substances are all conventional inorganic builders such as aluminosilicates, silicates, carbonates and phosphates.

Examples of suitable inorganic builders are aluminosilicates with ion-exchanging properties such as zeolites. Various types of zeolites are suitable, in particular zeolite A, X, B, P, MAP and HS in their Na form or in forms in which Na is partly replaced by other cations such as Li, K, Ca, Mg or ammonium. Suitable zeolites are described, for example, in EP-A 038 591, EP-A 021 491, EP-A 087 035, U.S. Pat. No. 4,604,224, GB-A 2 013 259, EP-A 522 726, EP-A 384 070 and WO-A 94/24 251.

Examples of other suitable inorganic builders are amorphous or crystalline silicates such as amorphous disilicates, crystalline disilicates such as the sheet silicate SKS-6 (manufactured by Hoechst). The silicates can be employed in the form of their alkali metal, alkaline earth metal or ammonium salts. Na, Li and Mg silicates are preferably employed.

Anionic surfactants

Examples of suitable anionic surfactants are fatty alcohol sulfates of fatty alcohols with 8 to 22, preferably 10 to 18, carbon atoms, eg. $C_9$–$C_{11}$-alcohol sulfates, $C_{12}$–$C_{13}$-alcohol sulfates, cetylsulfate, myristylsulfate, palmitylsulfate, stearylsulfate and tallow fatty alcohol sulfate.

Other suitable anionic surfactants are sulfated ethoxylated $C_8$–$C_{22}$-alcohols (alkyl ether sulfates) and their soluble salts. Compounds of this type are prepared, for example, by firstly alkoxylating a $C_8$–$C_{22}$, preferably a $C_{10}$–$C_{18}$-alcohol, eg. a fatty alcohol, then sulfating the alkoxylation product. Ethylene oxide is preferably used for the alkoxylation, employing from 2 to 50, preferably 3 to 20, mol of ethylene oxide per mole of fatty alcohol. The alcohols can, however, also be alkoxylated with propylene oxide, alone or with butylene oxide. Also suitable are those alkoxylated $C_8$–$C_{22}$-alcohols which contain ethylene oxide and propylene oxide or ethylene oxide and butylene oxide. The alkoxylated $C_8$–$C_{22}$-alcohols may contain the ethylene oxide, propylene oxide and butylene oxide units in the form of blocks or in random distribution.

Other suitable anionic surfactants are alkanesulfonates such as $C_8$–$C_{24}$, preferably $C_{10}$–$C_{18}$-alkanesulfonates, and the soaps such as the salts of $C_8$–$C_{24}$-carboxylic acids. Other suitable anionic surfactants are linear $C_9$–$C_{20}$-alkylbenzenesulfonates (LAS).

The anionic surfactants are preferably added in the form of salts to the detergent. Suitable cations in these salts are alkali metal ions such as sodium, potassium and lithium and ammonium ions such as hydroxyethylammonium, di(hydroxyethyl)ammonium and tri(hydroxyethyl) ammonium ions.

Nonionic surfactants

Examples of suitable nonionic surfactants are alkoxylated $C_9$–$C_{22}$-alcohols such as fatty alcohol alkoxylates or oxo alcohol alkoxylates. The alkoxylation can be carried out with ethylene oxide, propylene oxide and/or butylene oxide. All alkoxylated alcohols which contain at least two molecules of an abovementioned alkylene oxide in the adduct can be employed as surfactant in this case. Also suitable in this case are block copolymers of ethylene oxide, propylene oxide and/or butylene oxide, or adducts which contain said alkylene oxides in random distribution. From 2 to 50, preferably 3 to 20, mol of at least one alkylene oxide are used per mole of alcohol. Ethylene oxide is preferably employed as alkylene oxide. The alcohols preferably have 10 to 18 carbon atoms.

Another class of suitable nonionic surfactants comprises alkylphenol ethoxylate with $C_6$–$C_{14}$-alkyl chains and 5 to 30 mol of ethylene oxide units.

Another class of nonionic surfactants comprises alkyl polyglucosides with 8 to 22, preferably 10 to 18, carbon atoms in the alkyl chain. These compounds usually contain from 1 to 20, preferably 1.1 to 5, glucoside units.

Another class of nonionic surfactants comprises N-alkylglucamides of the structure II or III (II)

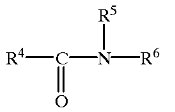

(III)

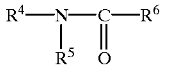

where $R^4$ is $C_6$–$C_{22}$-alkyl, $R^5$ is H or $C_1$–$C_4$-alkyl and $R^6$ is a polyhydroxyalkyl radical with 5 to 12 carbon atoms and at least 3 hydroxyl groups. It is preferred for $R^4$ to be $C_{10}$–$C_{18}$-alkyl, $R^5$ to be methyl and $R^6$ to be a $C_5$ or $C_6$ radical. Compounds of this type are obtained, for example, by acylating reductively aminated sugars with chlorides of $C_{10}$–$C_{18}$-carboxylic acids.

The detergents according to the invention preferably contain $C_{10}$–$C_{16}$-alcohols ethoxylated with 3–12 mol of ethylene oxide, particularly preferably ethoxylated fatty alcohols, as nonionic surfactants.

Organic cobuilders

Examples of suitable low molecular weight polycarboxylates as organic cobuilders are:

$C_4$–$C_{20}$-di-, -tri- and -tetracarboxylic acids such as succinic acid, propanetricarboxylic acid, butanetetracarboxylic acid, cyclopentanetetracarboxylic acid and alkyl- and alkylenesuccinic acids with $C_2$–$C_{16}$-alkyl and -alkylene radicals respectively;

$C_4$–$C_{20}$-hydroxy carboxylic acids such as malic acid, tartaric acid, gluconic acid, glutaric acid, citric acid, lactobionic acid and sucrosemono-, -di- and -tricarboxylic acids;

amino polycarboxylates such as nitrilotriacetic acid, methylglycinediacetic acid, alaninediacetic acid, ethylenediaminetetraacetic acid and serinediacetic acid;

salts of phosphonic acids such as hydroxyethanediphosphonic acid, ethylenediaminetetra(methylenephosphonate) and diethylenetriaminepenta(methylenephosphonate).

Examples of suitable oligomeric or polymeric polycarboxylates as organic cobuilders are:

oligomaleic acids as described, for example, in EP-A 451508 and EP-A 396303;

co- and terpolymers of unsaturated $C_4$–$C_8$-dicarboxylic acids, possible comonomers being monoethylenically unsaturated monomers from group (i) in amounts of up to 95% by weight from group (ii) in amounts of up to 60% by weight from group (iii) in amounts of up to 20% by weight Examples of suitable unsaturated $C_4$–$C_8$-dicarboxylic acids in this case are maleic acid, fumaric acid, itaconic acid and citraconic acid. Maleic acid is preferred.

Group (i) comprises monoethylenically unsaturated $C_3$–$C_8$-monocarboxylic acids such as acrylic acid, methacrylic acid, crotonic acid and vinylacetic acid. Preferably employed from group (i) are acrylic acid and methacrylic acid.

Group (ii) comprises monoethylenically unsaturated $C_2$–$C_{22}$-olefins, vinyl alkyl ethers with $C_1$–$C_8$-alkyl groups, styrene, vinyl esters of $C_1$–$C_8$-carboxylic acids, (meth) acrylamide and vinylpyrrolidone. Preferably employed from group (ii) are $C_2$–$C_6$-olefins, vinyl alkyl ethers with $C_1$–$C_4$-alkyl groups, vinyl acetate and vinyl propionate.

Group (iii) comprises (meth)acrylic esters of $C_1$–$C_8$-alcohols, (meth)acrylonitrile, (meth)acrylamides of $C_1$–$C_8$-amines, N-vinylformamide and vinylimidazole.

If the group (ii) monomers include vinyl esters, these can also be partially or completely hydrolyzed to vinyl alcohol structural units in the polymer. Suitable co- and terpolymers are disclosed, for example, in U.S. Pat. No. 3,887,806 and DE-A 43 13 909.

Suitable copolymers of dicarboxylic acids as organic cobuilders are, preferably:

copolymers of maleic acid and acrylic acid in the ratio 10:90 to 95:5 by weight, particularly preferably those in the ratio 30:70 to 90:10 by weight, with molecular weights of from 10,000 to 150,000;

terpolymers of maleic acid, acrylic acid and a vinyl ester of a $C_1$–$C_3$-carboxylic acid in the ratio 10 (maleic acid):90 (acrylic acid+vinyl ester) to 95 (maleic acid):10 (acrylic acid+vinyl ester) by weight, it being possible for the ratio of acrylic acid to vinyl ester to vary in the range from 20:80 to 80:20 by weight, and particularly preferably terpolymers of maleic acid, acrylic acid and vinyl acetate or vinyl propionate in the ratio 20 (maleic acid):80 (acrylic acid+vinyl ester) to 90 (maleic acid):10 (acrylic acid+vinyl ester) by weight, it being possible for the ratio of acrylic acid to vinyl ester to vary in the range from 30:70 to 70:30 by weight;

copolymers of maleic acid with $C_2$–$C_8$-olefins in the molar ratio 40:60 to 80:20, with particularly preferred copolymers being those of maleic acid with ethylene, propylene or isobutene in the molar ratio 50:50.

Graft copolymers of unsaturated carboxylic acids on low molecular weight carbohydrates or hydrogenated carbohydrates, cf. U.S. Pat. No. 5,227,446, DE-A 4415623, DE-A 4313909, are likewise suitable as organic cobuilders.

Examples of suitable unsaturated carboxylic acids in this case are maleic acid, fumaric acid, itaconic acid, citraconic acid, acrylic acid, methacrylic acid, crotonic acid and vinylacetic acid, and mixtures of acrylic acid and maleic acid, or are grafted on in amounts of from 40 to 95% of the weight of the component to be grafted.

It is additionally possible, for modification, for up to 30% by weight, based on the component to be grafted, of other monoethylenically unsaturated monomers to be present in the polymer. Suitable modifying monomers are the group (ii) and (iii) monomers mentioned above.

Suitable as grafting base are degraded polysaccharides such as acidically or enzymatically degraded starches, inulins or cellulose, reduced (hydrogenated or reductively aminated) degraded polysaccharides such as mannitol, sorbitol, aminosorbitol and glucamine, and polyalkylene glycols with molecular weights of up to $M_w$=5000, eg. polyethylene glycols, ethylene oxide/propylene oxide or ethylene oxide/butylene oxide block copolymers, random ethylene oxide/propylene oxide or ethylene oxide/butylene oxide copolymers, alkoxylated mono- or polyhydric $C_1$–$C_{22}$-alcohols, cf. U.S. Pat. No. 4,746,456.

Preferably employed from this group are grafted degraded or degraded reduced starches and grafted polyethylene oxides, employing from 20 to 80% of monomers based on the weight of the grafting component in the graft copolymerization. A mixture of maleic acid and acrylic acid in the ratio from 90:10 to 10:90 by weight is preferably employed for the grafting.

Polyglyoxylic acids are described as organic cobuilders, for example in EP-B 001004, U.S. Pat. No. 5,399,286, DE-A 4106355 and EP-A 656914. The end groups of the polyglyoxylic acids may have different structures.

Polyamido carboxylic acids and modified polyamidocarboxylic acids are disclosed as organic cobuilders, for example, in EP-A 454126, EP-B 511037, WO-A 94/01486 and EP-A 581452.

Also preferably used as organic cobuilders are polyaspartic acid or cocondensates of aspartic acid with other amino acids, $C_4$–$C_{25}$-mono- or -dicarboxylic acids and/or $C_4$–$C_{25}$-mono- or -diamines. Polyaspartic acids modified with $C_6$–$C_{22}$-mono- or -dicarboxylic acids or with $C_6$–$C_{22}$-mono- or -diamines and prepared in phosphorus-containing acids are particularly preferably employed.

Condensates of citric acid with hydroxy carboxylic acids or polyhydroxy compounds are disclosed as organic cobuilders, for example, in WO-A 93/22362 and WO-A 92/16493. Condensates containing carboxyl groups of this type normally have molecular weights of up to 10,000, preferably up to 5000.

Antiredeposition agents and soil-release polymers

Suitable soil-release polymers and/or antiredeposition agents or detergents are, for example:

polyesters from polyethylene oxides with ethylene glycol and/or propylene glycol and aromatic dicarboxylic acids or aromatic and aliphatic dicarboxylic acids;

polyesters from polyethylene oxides with di- and/or polyhydric alcohols and dicarboxylic acids which are endgroup-capped at one end.

Polyesters of this type are disclosed, for example, in U.S. Pat. No. 3,557,039, GB-A 1154730, EP-A 185427, EP-A 241984, EP-A 241985, EP-A 272033 and U.S. Pat. No. 5,142,020.

Further suitable soil-release polymers are amphiphilic graft or other copolymers of vinyl and/or acrylic esters on polyalkylene oxides (cf. U.S. Pat. No. 4,746,456, U.S. Pat. No. 4,846,995, DE-A 3711299, U.S. Pat. No. 4,904,408, U.S. Pat. No. 4,846,994 and U.S. Pat. No. 4,849,126) or modified celluloses such as methylcellulose, hydroxypropylcellulose or carboxymethylcellulose.

Color-transfer inhibitors

Examples of color-transfer inhibitors employed are homo- and copolymers of vinylpyrrolidone, vinylimidazole, vinyloxazolidone and of 4-vinylpyridine N-oxide with molecular weights of from 15,000 to 100,000, and crosslinked fine-particle polymers based on these monomers. The use mentioned here of such polymers is known, cf. DE-B 2232353, DE-A 2814287, DE-A 2814329 and DE-A 4316023.

Enzymes

Suitable enzymes are proteases, lipases, amylases and cellulases. The enzyme system may be confined to a single one of the enzymes or comprise a combination of various enzymes.

Bleach catalysts

Suitable bleach catalysts are quaternized imines and sulfone imines (cf. U.S. Pat. No. 5,360,568, U.S. Pat. No. 5,360,569 and EP-A 453003) and manganese complexes (cf. WO-A 94/21777).

Use in detergents and bleaches for textile laundering

The present invention also relates to detergents and bleaches for textile laundering which contain from 0.1 to 20% by weight, preferably 0.5 to 10% by weight, based on the total amount of the formulation, of one or more heterocyclic compounds I.

Typical textile detergents and bleaches of these types are approximately the following composition:

0.5–20, preferably 5–15,% by weight of anionic and/or nonionic surfactants, 0.5–60, preferably 5–40,% by weight of builders from the group consisting of condensed phosphates, alkali metal silicates, alkali metal carbonates, sodium aluminum silicates and mixtures thereof, 0–20, preferably 0.5–8,% by weight of builders from the group consisting of salts of amino carboxylic acids, salts of polyphosphonic acids, salts of polycarboxylic acids and mixtures thereof, 2–35, preferably 5–30,% by weight of inorganic peroxy compounds, 0.1–20, preferably 0.5–10,% by weight of compounds I, ad 100% conventional auxiliaries and accompanying substances and water.

The activators I according to the invention are preferably employed in powder or granular detergents. These may be conventional heavy duty detergents or concentrated or compacted detergents.

A typical powder or granular heavy-duty detergent according to the invention may have the following composition, for example:

0.5–50, preferably 5–30,% by weight of at least one anionic and/or nonionic surfactant, 0.5–60, preferably 15 to 40,% by weight of at least one inorganic builder, 0–20, preferably 0.5–8,% by weight of at least one organic cobuilder, 2–35, preferably 5–30,% by weight of at least one inorganic bleach, in particular perborate or percarbonate, 0.1–20, preferably 0.5–10,% by weight of a bleach activator according to the invention, possibly mixed with other bleach activators, 0–1, preferably up to a maximum of 0.5,% by weight of a bleach catalyst, 0–5% by weight, preferably 0–2.5% by weight, of a polymeric color-transfer inhibitor, 0–1.5% by weight, preferably 0.1–1.0% by weight, of protease, 0–1.5% by weight, preferably 0.1–1.0% by weight, of other detergent enzymes, in particular lipase, 0–1.5% by weight, preferably 0.2–1.0% by weight, of a soil-release polymer, ad 100% conventional auxiliaries and additives and water.

Inorganic builders preferably employed in detergents are sodium carbonate, sodium bicarbonate, zeolite A and P, and amorphous and crystalline Na silicates, in particular sheet silicates such as SKS-6 (manufactured by Hoechst AG).

Organic cobuilders preferably employed in detergents are acrylic acid/maleic acid copolymers, acrylic acid/maleic acid/vinyl ester terpolymers such as acrylic acid/maleic acid/vinyl acetate terpolymers, polyaspartic acid and citric acid.

Inorganic bleaches preferably employed in detergents are sodium perborate and sodium carbonate perhydrate.

Inorganic surfactants preferably employed in detergents are fatty alcohol sulfates, linear alkylbenzenesulfonates (LAS) and soaps, with the LAS content preferably being below 8% by weight, particularly preferably below 4% by weight.

Nonionic surfactants preferably employed in detergents are $C_{11}$–$C_{17}$ oxo alcohol ethoxylates with 3–13 ethylene oxide units, $C_{10}$–$C_{16}$ fatty alcohol ethoxylates with 3–13 ethylene oxide units, and ethoxylated fatty or oxo alcohols additionally alkoxylated with 1–4 propylene oxide or butylene oxide units.

Enzymes preferably employed in detergents are protease, lipase and cellulase. The amounts of commercial enzymes added to the detergent are, as a rule, from 0.1 to 1.5% by weight, preferably 0.2 to 1.0% by weight, of the formulated enzyme. Examples of suitable proteases are Savinase and Esperase (manufactured by Novo Nordisk). An example of a suitable lipase is Lipolase (manufactured by Novo Nordisk). An example of a suitable cellulase is Celluzym (manufactured by Novo Nordisk).

Antiredeposition agents and soil-release polymers preferably employed in detergents are graft copolymers of vinyl acetate on polyethylene oxide of molecular weight 2500–8000 in the ratio from 1.2:1 to 3.0:1 by weight, polyethylene terephthalate/oxyethylene terephthalates of molecular weight 3000 to 25,000 from polyethylene oxides of molecular weight 750 to 5000 with terephthalic acid and ethylene oxide and a molar ratio of polyethylene terephthalate to polyoxyethylene terephthalate from 8:1 to 1:1, and block polycondensates disclosed in DE-A 4403866.

Color-transfer inhibitors preferably employed in detergents are soluble vinylpyrrolidone and vinylimidazole copolymers with molecular weights above 25,000, and fine-particle crosslinked polymers based on vinylimidazole.

The described detergents preferably contain phosphonates.

The powder or granular detergents according to the invention may contain up to 60% by weight of inorganic fillers. Sodium sulfate is normally used for this purpose. However, the detergents according to the invention preferably contain no more than 20% by weight, particularly preferably no more than 8% by weight, of fillers.

The detergents according to the invention may have apparent densities varying in the range from 300 to 1200, in particular 500 10 to 950 g/l. As a rule, modern compact detergents have high apparent densities and a granular structure.

Besides combined detergents and bleaches, suitable formulations of the described activators for textile laundering are also compositions which are used as additives to peroxide-containing or peroxide-free detergents. They essentially contain an activator or a mixture of activator and peroxy compound and, where appropriate, other auxiliaries and additives, especially stabilizers, pH regulators, thickeners and surfactants.

The present invention also relates to bleach additives for textile laundering which contain from 1 to 30% by weight, preferably 5 to 25% by weight, based on the total amount of the additive formulation, of one or more heterocyclic compounds I.

Typical bleach additives of this type have approximately the following composition:

5–50, preferably 15–35,% by weight of inorganic peroxy compound,

1–30, preferably 5–25,% by weight of compounds I,

0–5, preferably 0.1–3,% by weight of peroxide stabilizers,

0–40, preferably 5–30,% by weight of pH regulators, ad 100% by weight other conventional auxiliaries and additives.

Compositions intended for cleaning hard surfaces contain, besides peroxy compound and activator, in particular surfactants, builders and, in the case of polishing and scouring compositions, ingredients with an abrasive action. Since these compositions are frequently used at room temperature, in this case the use of the activators according to the invention has a particularly advantageous effect on the bleaching and germicidal action.

Formulations used in disinfection have particular significance because in general greater demands are made on safety of use in this case. Disinfectants based on the described activators contain, besides the latter and inorganic peroxy compounds in general also further auxiliaries and additives such as pH regulators, stabilizers and surfactants. In special cases they may additionally contain specific microbicides which enhance the lethal action, which is very extensive per se, of the activated peroxy compound for particular germs.

The present invention also relates to disinfectants which contain from 1 to 40% by weight, preferably 5 to 30% by weight, based on the total amount of the formulation, of one or more heterocyclic compounds I.

Typical disinfectants of this type have approximately the following composition:

5–40, preferably 10–20,% by weight of inorganic peroxy compounds,

1–40, preferably 5–30,% by weight of compounds I,

0–5, preferably 0.1–3,% by weight of peroxide stabilizers, 0.1–20, preferably 0.2–5,% by weight of surfactants, ad 100% by weight further auxiliaries and additives.

The use according to the invention of the described activators is, however, by no means restricted to use in formulations of the types described or others. Thus, for example, in the commercial sector priority is generally given to metering reagents singly because this often represents the less costly method.

Most of the heterocyclic compounds I are disclosed in the literature, and the syntheses for preparing them are described.

It is possible with the heterocyclic compounds I to achieve a distinct improvement in the bleaching, oxidizing and cleaning action in the lower temperature range in the technical applications described.

EXAMPLES

Typical preparation methods for heterocyclic compounds I

Example 1

40 Preparation of O-benzoylpantolactone 0.5 mol of pantolactone (64.5 g) was dissolved in 500 ml of toluene in a flask with stirrer, thermometer, dropping funnel and condenser. 0.51 mol of triethylamine was added, and the mixture was heated to 50° C. Then, at this temperature, 0.51 mol of benzoyl chloride (70.3 g) was added dropwise at such a rate that the temperature did not exceed 70° C. The mixture was stirred at 70 ° C. for 1 hour and then cooled to 20 ° C. It was subsequently washed twice with 400 ml of water and once with 400 ml of saturated $NaHCO_3$ solution. The organic phase was separated off and dried over mag- nesium sulfate. Removal of the solvent by distillation resulted in 102.6 g (88%) of O-benzoylpentolactone (purity >90% by $^1$H-NMR).

Example 2

Preparation of O-octanoylpantolactone

Prepared from pentolactone and octanoyl chloride as in Example 1.

Example 3

Preparation of N-octanoyl-2-oxazolidone 87 g (1.0 mol) of 2-oxazolidone and 185 g of tributylamine were dissolved in toluene at 80° C. in a 4 1 three-neck flask with stirrer, condenser, thermometer and nitrogen inlet. At this temperature, 1.03 mol of octanoyl chloride (3% excess) were added dropwise (over about 2 h). The mixture was then stirred at 80° C. for 1 h and cooled to 50° C. While stirring, 160 g of 25% by weight aqueous NaOH were added. Removal of the aqueous phase and washing with water (once) were followed by distillation to remove initially the toluene (1013 mbar/about 115° C.) and then the tributylamine (30 mbar/130° C.). A pale yellow oil was obtained and slowly crystallized. The product was recrystallized from acetone (content of product: 90% by $^1$H-NMR, yield: about 90% by weight).

Example 4

Preparation of N-pivaloyl-2-oxazolidone

Prepared from 2-oxazolidone and pivaloyl chloride $(H_3C)_3C$—COCl as in Example 3.

Example 5

Preparation of N-benzoyl-2-oxazolidone

Prepared from 2-oxazolidone and benzoyl chloride as in Example 3.

Example 6

Preparation of N,N'-carbonylbis-ϵ-caprolactam 1 mol (113 g) of ϵ-caprolactam and 1.05 mol (133.3 g) of dimethylcyclohexylamine (DMCA) were introduced into 700 ml of toluene in a 2 l flask with stirrer. Over the course of 45 min, 0.55 mol (54.5 g) of phosgene was passed into the reaction solution. The internal temperature was kept at about 20° C. using an ice bath. After the addition of phosgene was complete, the reaction mixture was heated to 40° C. and stirred at this temperature for 2 h. The DMCA hydrochlorid which had formed was removed by filtration and washed with toluene. The organic phase was extracted with 250 ml of water and then concentrated. The title compound was obtained in a yield of 46% (58 g) with a melting point of 116° C.

Example 7

Preparation of N-(phenyloxycarbonyl)-γ-butyrolactam

The title compound was prepared by customary methods from phenyl chloroformate and γ-butyrolactam (2-pyrrolidone).

Examples of Use

Examples 2, 4, 5 and 6 were used in washing tests with test soilings with red wine, tea or grass on cotton fabric, and the bleaching actions achieved were in most cases better than with the activator N,N,N',N'-tetraacetylethylenediamine (TAED) which represents the prior art (Comparative Examples A and B). Examples 6 and B were used not only in washing tests with a test soiling of grass on cotton but also with a colored fabric (EMPA 115). It is evident from the colored fabric that the unwanted bleaching of the coloring with activators used according to the invention is comparable to or at a lower level than TAED.

The tests were carried out in a Launder-O-meter, Atlas standard type, using a phosphate-free heavy duty detergent I under the following conditions:

Liquor volume 250 ml

Fabric: 4×2.5 g of various test fabrics (bleached cotton soiled with red wine, tea or grass, and EMPA 115 colored fabric)

Water hardness 3 mmol/l (170 German hardness)

Temperatures: 22° C. and 38° C., or 38° C. and 60° C.

Washing time: 30 min (including heating time)

Rinsing: 3×30 sec with tap water (14 German hardness)

Detergent dose: 7.0 g/l

Detergent composition I (% by weight):

| | | |
|---|---|---|
| Linear alkylbenzenesulfonate (Na salt) | | 6.25 |
| $C_{13}/C_{14}$ oxo alcohol reacted with 7 mol of ethylene oxide | | 4.7 |
| Tallow fatty soap | | 2.8 |
| Zeolite A | | 25.0 |
| Sodium carbonate | | 12.0 |
| Magnesium silicate | | 1.0 |
| Sodium disilicate | | 4.5 |
| Polycarboxylate (acrylic acid/methacrylic acid 60:40, $M_W$ = 70,000) | | 3.0 |
| Carboxymethylcellulose (60%) | | 1.0 |
| Sodium perborate monohydrate | | 10.0 |
| Activator (100% active substance) | 0 or | 4.0 |
| Sodium sulfate | to | 100 |

The tests were evaluated by measuring the reflectance of the dried fabrics at a wavelength of 460 nm. The reflectance differences $\Delta R=R_A-R_O$ between the fabrics washed without activator and those washed with activator for the four test fabrics and at the stated washing temperatures are shown in the following Table 1.

TABLE 1

| | Test fabric with | | | |
|---|---|---|---|---|
| | red wine soiling | | tea soiling | |
| Activator | 22° C. | 38° C. | 22° C. | 38° C. |
| Example No. 2 | 3.5 | 3.7 | 10.1 | 9.5 |
| Example No. 4 | 2.8 | 6.4 | 11.4 | 9.0 |
| Example No. 5 | 3.3 | 10.7 | 16.1 | 11.5 |
| (A) for comp.: TAED | 3.8 | 6.5 | 9.3 | 7.5 |

| | Test fabric with | | | |
|---|---|---|---|---|
| | grass soiling | | colored fabric (EMPA 115) | |
| Activator | 38° C. | 60° C. | 38° C. | 60° C. |
| Example No. 6 | 2.0 | 1.4 | 1.3 | 1.9 |
| (B) for comp.: TAED | 0.5 | 0.4 | 1.0 | 2.0 |

(EMPA 115: Test fabric No. 115 from the Eidgenössische Material-prüfungsanstalt, Switzerland)

Further washing tests were carried out with Examples 6 and 7 on test soilings of tea or red wine on cotton fabric, and the bleaching actions achieved were in most cases better than with TAED (comparative Examples C and D).

Table 2 which follows shows typical modern heavy duty detergent formulation quantities II to VIII. Of these, compositions IV and V were employed in the washing tests.

TABLE 2

| Compositions of heavy duty detergents (% by weight) | | | | | | | |
|---|---|---|---|---|---|---|---|
| | II | III | IV | V | VI | VII | VIII |
| PVP (K value 30) | 1.5 | | | | | | |
| VI/VP copolymer (K value 30) | | 1.0 | | | 1.0 | 0.6 | |
| AA/MA (70000) | | | 5.0 | | | | 5.0 |
| AA/MA/VAc terpolymer (20000) | | | | | | 5.0 | |
| Oligomaleic acid | | | | | 5.0 | | |
| Polyaspartic acid | 7.5 | | | | | | |
| Na perborate monohydrate | 15 | 15 | | | 15 | | 7.5 |
| Na perborate | | | 18 | 15 | | 18 | |
| Activator of Example 7 | | 3.8 | | 5.0 | | 4.2 | 2.0 |
| Activator of Example 6 | 4.0 | | 5.0 | | 2.9 | | |
| Na lauryl sulfate | 3.5 | 6.0 | 12.0 | 6.0 | 5.5 | 2.0 | |
| Linear alkylbenzenesulfonate Na salt | | 1.7 | 0.8 | | | 4.5 | |
| Soap | 2.8 | 0.6 | 0.4 | 2.5 | 1.5 | | 2.4 |
| C13/C15 oxo alcohol* 3EO | | 3.0 | | | | | |
| C13/C15 oxo alcohol* 7EO | 4.7 | | 4.7 | 13.5 | 4.0 | 6.5 | |
| C13/C15 oxo alcohol* 10EO | | 3.0 | | | | | |
| C12/C14 fatty alcohol* 7EO | | | | | | | 10.0 |
| Lauryl alcohol* 13EO | | | | | | 5.0 | |
| Zeolite A | 25 | 25 | 15 | | 30 | 15 | 35 |
| Zeolite P | | | | 40 | | | |
| SKS-6 | | | 14 | | | 15 | |
| Na disilicate | 2.5 | 3.9 | | 0.5 | 4.5 | | 1.5 |
| Mg silicate | 1.0 | | 0.8 | | 1.0 | 1.0 | 0.6 |
| Sodium sulfate | 20 | 2.5 | 3.2 | 2.0 | 1.5 | 5.5 | 3.4 |
| Sodium bicarbonate | | | 9.0 | 6.5 | | | |
| Sodium carbonate | 12.0 | 13.6 | | | 10.0 | 8.0 | 9.8 |
| Soil-release polymer | | 0.4 | | | 0.5 | | |
| Polyethylene terephthalate/oxyethylene terephthalate | 1.0 | | | 0.5 | 0.8 | 1.0 | |
| Carboxymethylcellulose | 0.6 | 1.3 | 0.6 | 1.0 | 0.6 | 0.6 | 0.5 |
| Dequest ® 2046 | | | | 0.5 | | | |
| Citric acid | | 6.8 | 5.0 | | | 2.5 | 3.8 |
| Lipase | | | | | 1.0 | | |
| Protease | | 1.0 | | | 1.0 | 0.5 | 0.6 |
| Cellulase | | | | | | | 0.6 |
| Water | to 100 | to 100 | to 100 | to 100 | to 100 | to 100 | to 100 |

| | |
|---|---|
| SKS-6 = | commercial sheet silicate (manufactured by Hoechst AG) |
| Soil-release polymer = | graft copolymer of vinyl acetate on polyethylene glycol of molecular weight 6000, molecular weight of graft copolymer 24000 |
| Dequest ® 2046 = | ethylenediamine-N,N,N',N'-tetra-(methylenephosphonate) |

The test was carried out under the following washing conditions:

| | |
|---|---|
| Machine | Launder-O-meter, Atlas standard type |
| Cycles | 1 |
| Time | 30 min |
| Temperatures | 22° C., 38° C. and 60° C. |
| Water hardness | 3.0 mmol/1 |
| Test fabrics | 5 × 2.5 g of various test fabrics (bleached cotton or cotton cheesecloth soiled with red wine or tea) |
| Amount of liquor | 250 ml |
| Liquor ratio | 1:20 |
| Detergent concentration | 4.5 g/l |

The color strength of the test fabrics was measured by photometry. The particular color strengths of the test soilings before and after the washing were determined, and the absolute bleaching action Aabs was calculated therefrom in percent, from the reflectances measured on the individual test fabrics at 18 wavelengths in the range from 400 to 700 nm at 20 nm intervals by the method described in A. Kud, Seifen, Öle, Fette Wachse 119, (1993) 590–594.

TABLE 3

| Results of washing tests with soiled test fabrics (numbers are absolute bleaching action $A_{abs}$ in %) | | | | | |
|---|---|---|---|---|---|
| Bleach | Detergent | Tea | | Red wine | |
| activator | formulation | 22° C. | 38° C. | 22° C. | 38° C. |
| Ex. No. 6 | V | 31.3 | 61.4 | 68.4 | 74.9 |
| (C) for comp.: TAED | V | 21.8 | 55.5 | 64.1 | 75.6 |
| without activator | V | 4.4 | 10.9 | 55.3 | 56.8 |
| Ex. No. 7 | IV | 73.3 | 82.6 | 75.9 | 84.4 |
| (D) for comp.: TAED | IV | 64.1 | 80.6 | 69.8 | 85.1 |
| Without activator | IV | 44.2 | 60.7 | 54.2 | 64.6 |

The results in Tab. 3 show that the bleaching action of the carbonyllactam derivatives from Examples 6 and 7 to be used according to the invention exceeds that of TAED distinctly in some cases, especially at low temperatures. Carbonylcaprolactam derivatives are also mostly distinctly more effective than TAED for grass soilings.

We claim:

1. A process for activating inorganic peroxy compounds, comprising contacting an inorganic peroxy compound with an activator having the formula (1):

$$L—X—L \qquad (I)$$

wherein each L is a heterocyclic radical identical to the other and each is:

(a) a cyclic carbamate residue of the formula:

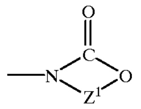

(b) a lactonoxy residue of the formula:

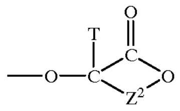

or (c) a lactam residue of the formula:

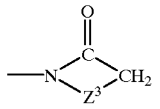

wherein $Z^1$, $Z^2$ and $Z^3$ are each, independently, a 1,2-, 1,3-, 14-, or 1,5-alkylene group which has 2 to 20 carbon atoms and which is optionally substituted by one to three moieties selected from the group consisting of hydroxyl, $C_1$–$C_4$-alkoxy, amino, $C_1$–$C_4$-alkylamino, di-$C_1$–$C_4$-alkylamino, chlorine, bromine, nitro, cyano, carboxyl, sulfo, carboxy-$C_1$–$C_4$-alkyl, carboxamide, phenyl, tolyl and benzyl, wherein aromatic nuclei of said phenyl, tolyl or benzyl radical are optionally substituted by said moieties, and said 1,2-, 1,3-, 1,4-, or 1,5-alkylene group is optionally interrupted by one or two non-adjacent oxygen atoms, amino groups, $C_1$–$C_4$-alkylamino groups or carbonyl groups:

T is hydrogen or $C_1$–$C_4$-alkyl; and

X is an oxygen-containing group of the formula:

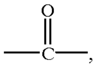, 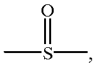, 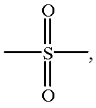, or 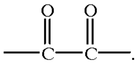.

2. The process as claimed in claim 1, wherein X is

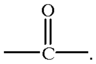.

3. The process as claimed in claim 1, wherein the inorganic peroxy compound and the activator are contacted at a temperature of from 10° C. to 80° C.

4. The process as claimed in claim 1, wherein the inorganic peroxy compound and the activator are contacted in an aqueous medium.

5. The process as claimed in claim 4, wherein the aqueous medium further comprises at least one detergent.

6. The process as claimed in claim 4, wherein the detergent is an anionic or nonionic surfactant.

7. The process as claimed in claim 1, wherein the inorganic peroxy compound is selected from the group consisting of hydrogen peroxide, sodium carbonate, sodium carbonate perhydrate, phosphate perhydrates and urea perhydrate.

8. The process as claimed in claim 1, wherein the inorganic peroxy compound and the activator are contacted in the presence of a textile, hair or hard surface, and the textile, hair or hard surface is bleached.

9. The process as claimed in claim 1, wherein X is

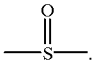.

10. The process as claimed in claim 1, wherein X is

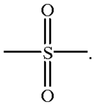.

11. The process as claimed in claim 1, wherein X is

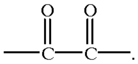.

12. The process as claimed in claim 1, wherein the inorganic peroxy compound and the activator are contacted at a temperature of from 15° to 60° C.

13. The process as claimed in claim 12 wherein the inorganic peroxy compound and the activator are contacted at a temperature of from 20° to 45° C.

* * * * *